US00RE37411B1

(19) United States
(12) Reissued Patent
Lieber et al.

(10) Patent Number: US RE37,411 E
(45) Date of Reissued Patent: Oct. 16, 2001

(54) EXPRESSION CASSETTE FOR ANTISENSE EXPRESSION OF RIBOZYME

(75) Inventors: Andre Lieber; Michael Strauss, both of Berlin (DE)

(73) Assignee: Max-Planck Gesellschaft (DE)

(21) Appl. No.: 09/089,594

(22) Filed: Jun. 2, 1998

Related U.S. Patent Documents

Reissue of:
(64) Patent No.: 5,695,992
Issued: Dec. 9, 1997
Appl. No.: 08/314,588
Filed: Sep. 28, 1994

(30) Foreign Application Priority Data

Jul. 4, 1994 (DE) ..... 44 24 761

(51) Int. Cl.[7] ..... C12Q 1/68; C12N 15/85

(52) U.S. Cl. ..... 435/320.1; 435/6; 435/91.31; 435/325; 536/23.1; 536/24.5

(58) Field of Search ..... 435/6, 91.31, 320.1, 435/325; 536/23.1, 24.5

*Primary Examiner*—Sean McGarry
*Assistant Examiner*—Andrew Wang
(74) *Attorney, Agent, or Firm*—Gabriel P. Katona L.L.P.

(57) ABSTRACT

The invention is an expression cassette for the antisense expression of ribozyme, having a strong promotor, suitably a T7 promotor, an adenoviral va-RNA gene, a stable loop region, and an insertion site for the antisense/ribozyme sequence in the loop region.

5 Claims, 2 Drawing Sheets

STRUCTURE OF RIBOZYME
5'UCCUCAGGAGUGGUCUUCGCCAACAGCC
AGGAGUCCUCACCA AAGCGGUUGUCGG 5'
988

PLASMID MATRICES FOR RIBOZYME SYNTHESIS
T7Rz
T7Rzneo
GvaRz
GvaLRz
T7
Rz
HindIII
neo
Va
circ.

ELECTROPHORETIC REPRESENTATION OF CLEAVAGE PRODUCTS
Rz plasmid
polymerase
T7
T7Rz
T7Rz neo
pd.III
GvaRz
GvaLRz
1663
988
675
1 2 3 4 5 6 7

EXPRESSION CASSETTE FOR ANTISENSE EXPRESSION OF RIBOZYME

Matter enclosed in heavy brackets [ ] appears in the original patent but forms no part of this reissue specification; matter printed in italics indicates the additions made by reissue.

FIELD OF THE INVENTION

The present invention relates to a vector for the antisense and for the ribozyme expression. The invention can be usefully employed in molecular biology, genetic engineering, and in medical applications.

BACKGROUND OF THE INVENTION

The inactivation of gene functions by reverse genetic material is the most important methods for switching off certain genes. This is of great importance for combating infectious and other diseases (including AIDS), caused by interference with gene expression. A gene function can be inactivated on various levels: by homologous recombination at the DNA level, by antisense nucleic acids or ribozymes on the RNA level, or by antibodies on the protein level. In conversion to practice, all four possibilities have advantages and disadvantages. For therapeutic applications, only the RNA inactivation by antisense molecules, or by ribozymes appears to be implementable. Both classes of compounds can be synthesized chemically or produced in conjunction with a promotor by biological expression in vitro or even in vivo. The principle of catalytic self-cleavage of RNA molecules and the cleavage in trans has become well established in the last 10 years. The hammerhead ribozymes are characterized best among the RNA molecules with ribozyme activity. Since it was shown that hammerhead structures can be integrated into heterologous RNA sequences and that ribozyme activity can thereby be transferred to these molecules, it seems clear that catalytic antisense sequences for almost any target sequence can be created, provided the target sequence contains a potential matching cleavage site.

The basic principle of constructing ribozymes is very simple. An interesting region of the RNA, which contains the GUC (or CUC) triplet, is selected. Two oligonucleotides strands, each with 6 to 8 nucleotides, are taken and the catalytic hammerhead sequence is inserted between them.

Molecules of this type were synthesized for numerous target sequences. They showed catalytic activity in vitro and in some cases also in vivo. The best results were obtained with short ribozymes and target sequences. A topical challenge for the in vivo application is the construction of ribozyme genes which permit a continuous expression of the ribozyme in a particular cell (Bertrand, E. et al., (1994) Nucleic Acids Res. 22, 293 to 300).

There are five possible reasons for interference with a satisfactory functioning of expressed ribozymes within the complex intracellular milieu.

1. The mRNA substrate exists within the cell presumably in a highly folded structure, which furthermore can also be protected by proteins bound to parts of the structure. The encountering of accessible sites within the substrate allowing for hybridization with the complementary flanking regions of the ribozyme is a question of actual probability. Computer-aided predictions of possible, thermodynamically stable secondary structures can be useful when searching for loop regions without base pairing. However, the physiological relevance of these conformation models is still uncertain.

2. Since the target mRNA is transported immediately out of the cell nucleus, the ribozyme must also enter the cytoplasm, preferably along the same path. It is, however, difficult to achieve a co-localization of ribozyme and its substrate.

3. The in vivo use of ribozymes requires the insertion of ribozyme genes in suitable expression cassettes. The transcription of these constructs can produce mRNAs, in which the central, catalytic, secondary structure of the ribozymes is displaced by other, more stable base pairings within the non-complementary flanking sequences.

4. 100- to 1,000-fold excess of ribozyme molecules relative to the target sequence is necessary for attaining a recordable increase in the RNA level. The production of $\mathbf{10}^5$ to $\mathbf{10}^6$ ribozymes per cell over a long period of time can, however, have cytotoxic effects. In general, such high expression levels are not stable. An excess of ribozymes is needed because of the inadequate stability of the ribozymes in the presence of nucleases, because of the ineffective transport to the cytoplasm and because of the less than optimum conversion factor of the cleavage reaction.

5. The kinetics of the cleavage reaction and the ability of the ribozymes to carry out multiple conversion reactions depends on the binding parameters and the structure of the complementary flanking regions of the ribozymes. Cellular proteins can affect the catalysis of the cleavage reaction, probably with the help of the dissociation of the ribozyme from the substrate of the cleavage reaction, which represents the preliminary step of the next cleavage reaction. Until now, it has not been possible to predict the optimum structure of the flanking regions for a ribozyme, to guarantee high specificity and high conversion. Despite many efforts to construct specific ribozyme genes, generally only partial successes have been achieved, mostly on the basis of trial and error experimentation.

DESCRIPTION OF THE INVENTION

It is an object of the present invention to construct a vector for antisense expression and ribozyme expression. The vector shall be able to result in a continuous and stable expression of a particular desired ribozyme or an antisense sequence in a cell.

This objective is realized with the construction of the expression cassette of the present invention, which has a strong promotor, suitably a T7 promotor, an adenoviral va-RNA gene, a stable loop region, and an insertion site for the antisense/ribozyme sequence in the loop region.

DESCRIPTION OF THE DRAWINGS

The present invention is described below in detail with reference being had to the drawing, wherein:

Thus, FIG. 1 shows the va-RNA gone at the site AatII into which the synthetic loop region was cloned. The ribozymes that are to be expressed are cloned between the PstI and SALI sites in the loop region. The symbolic box over the AatII site represents the sequence of the loop region, which is shown in the lower, right of FIG. 1 (open for the acceptance of ribozyme).

DETAILED DESCRIPTION OF THE INVENTION

The T7 promotor is suitably used in combination with T7 polymerase. The loop region is in a restriction site in the central part of the adenoviral va-RNA gene and its size is at least 2×21 bases of identical sequence. A suitable base sequence of the loop region is 5'-AACCCAGGTGTGCGACGTCAG-3' (Seq. Id. No. 1).

Figures 2A, 2B, 2C:
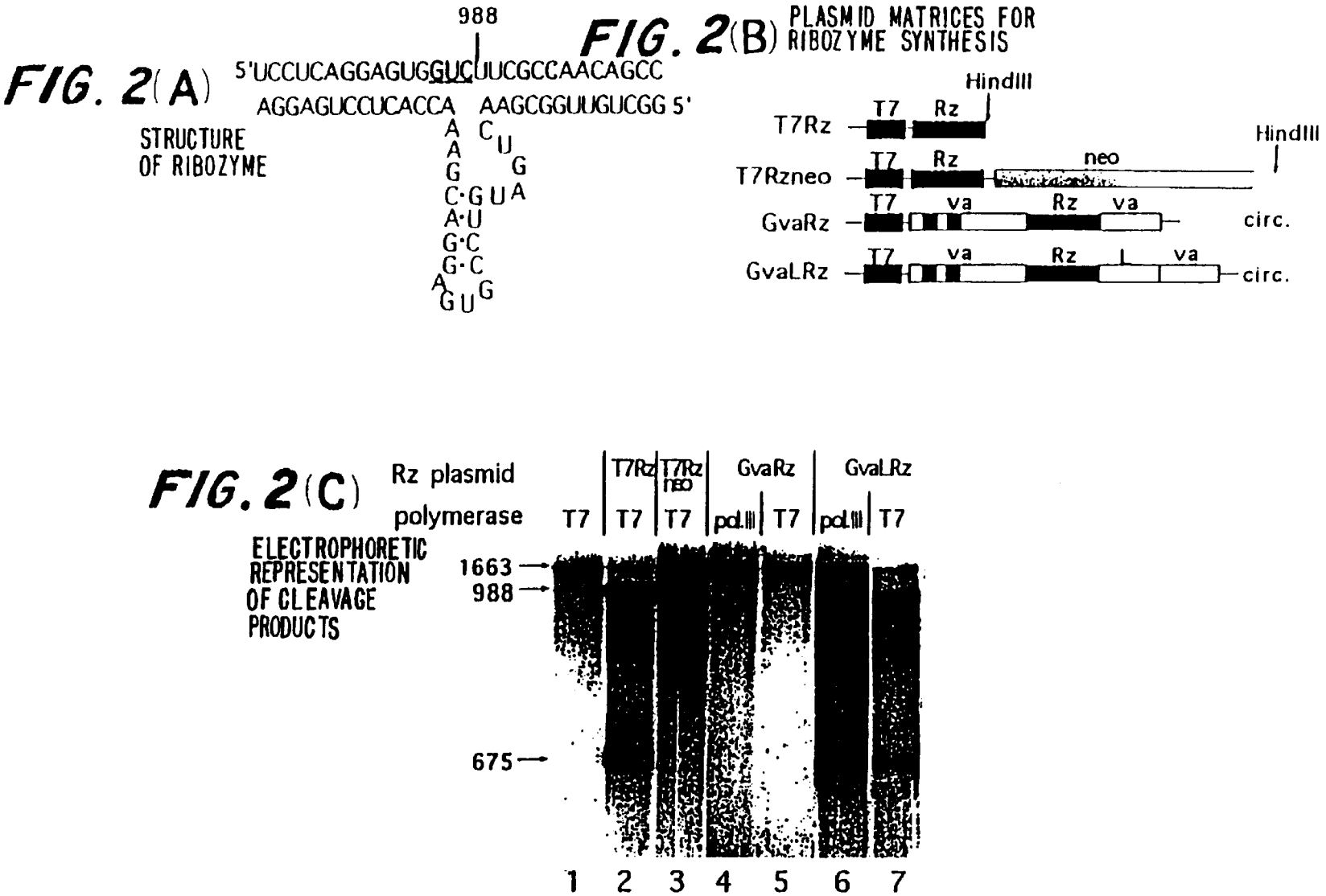
FIG. 2 shows the result of cleavage of hGH RNA (Seq. ID. No. 3) in vitro by a ribozyme, and the labelled parks A, B and C are described below.

The cleavage results of FIG. 2 also show (A) the structure of the specific ribozyme for a 27 n.t. region about the GUC at position 988 within the exon IV of hGH RNA;

(B) the maps of plasmid matrices for ribozyme synthesis by in vitro transcription with pol III (HeLa extract) and T7 RNA polymerase; and (C) an electrophoretic representation of the cleavage products.

The invention is further described by the following specific example.

EXAMPLE

The T7Rz and T7Rzneo plasmids were linearized by a Hind III treatment. GvaRz and GvaLRz were used in circular form. hGH RNA was synthesized from a linear (SstI section) of genomic hGH gene (1663 nt) by in vitro transcription with T7 RNA polymerase (with 0.2 $\mu Ci^{32}P$ of CTP/$\mu$g of RNA). An equimolar mixture (100 nM) of ribozyme and substrate was incubated at 37° C. in 50 mM of Tris-HCl of pH 7.5 and 10 mM of magnesium chloride for 30 minutes with prior heat denaturation (90 seconds at 95° C.). After the cleavage, the RNAs were purified and separated individually on a 6% polyacrylamide gel. Full-length RNA and ribozyme cleavage products (988 nt and 675 nt) were detected. The result shows that the embedding of the catalytic hammerhead structure in a stabilizing RNA (va) leads to a stable ribozyme, capable of functioning, only after the additional incorporation of the loop region.

SEQUENCE LISTING

```
(1) GENERAL INFORMATION:

   (iii) NUMBER OF SEQUENCES: 3


(2) INFORMATION FOR SEQ ID NO: 1:

     (i) SEQUENCE CHARACTERISTICS:
          (A) LENGTH: 21 base pairs
          (B) TYPE: nucleic acid
          (C) STRANDEDNESS: single
          (D) TOPOLOGY: linear

    (ii) MOLECULE TYPE: rRNA

    (xi) SEQUENCE DESCRIPTION: SEQ ID NO: 1:

AACCCAGGTG TGCGACGTCA G                                          21


(2) INFORMATION FOR SEQ ID NO: 2:

     (i) SEQUENCE CHARACTERISTICS:
          (A) LENGTH: 40 base pairs
          (B) TYPE: nucleic acid
          (C) STRANDEDNESS: single
          (D) TOPOLOGY: linear

    (ii) MOLECULE TYPE: rRNA

    (xi) SEQUENCE DESCRIPTION: SEQ ID NO: 2:

GGTTACCGCC CGCGTGTCGA ACCCAGGTGT GCGACGTCAG                      40


(2) INFORMATION FOR SEQ ID NO: 3:

     (i) SEQUENCE CHARACTERISTICS:
          (A) LENGTH: 28 base pairs
          (B) TYPE: nucleoside base
          (C) STRANDEDNESS: single
          (D) TOPOLOGY: linear

    (ii) MOLECULE TYPE: DNA (genomic)

    (xi) SEQUENCE DESCRIPTION: SEQ ID NO: 3:

UCCUCAGGAG UGGUCUUCGC CAACAGCC                                   28
```

Figure 1:
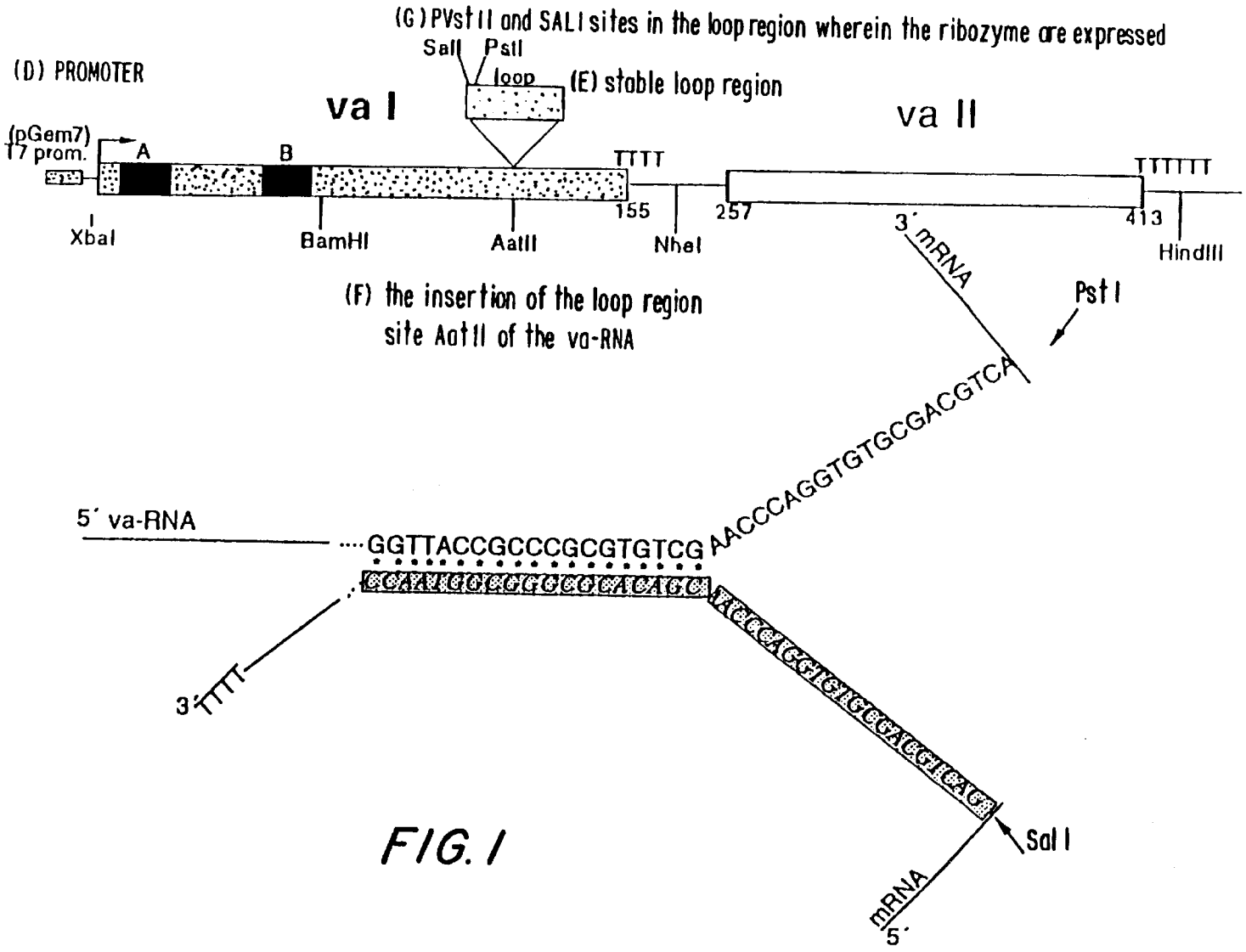
FIG. 1 shows the vaRNA genes, and the labelled parts show (D) the promotor, (E) the stable loop-region, and (F) the insertion site AatII of the loop region within the va-RNA, and (G) the PstI and SALI sites in the loop region wherein the ribozymes that are to be expressed are cloned (Seq. ID. No. 2).

We claim:

1. An antisense and ribozyme expression cassette which comprises a strong promotor, an adenoviral va-RNA gene having a central part, a stable loop region of a size of at least 2×21 base pairs of identical sequences, and an insertion site for the antisense/ribozyme sequence in the loop region, wherein said promotor, the adenoviral va-RNA gene, the loop region, and the insertion site are linked as shown in FIG. 1.

2. The expression cassette of claim 1, wherein said promotor is a T7 promotor.

3. The expression cassette of claim 2, wherein the T7 promotor is employed in combination with a T7 polymerase.

4. The expression cassette of claim 1, wherein said loop region is in a restriction site in the central part of the adenoviral va-RNA gene.

5. The expression cassette of claim 1, wherein said loop region contains twice the base sequence 5'-AACCCAGGTGTGCGACGTCAG-3' (Seq. Id. No. 1).

* * * * *